United States Patent [19]

Kaplan et al.

[11] Patent Number: 4,639,528
[45] Date of Patent: Jan. 27, 1987

[54] CRYSTALLINE FORM OF 7-(DIMETHYLAMINOMETHYLENE-AMINO-9A-METHOXYMITOSANE

[75] Inventors: Murray A. Kaplan, Syracuse; Dolatrai M. Vyas, Fayetteville, both of N.Y.

[73] Assignee: Bristol-Myers Company, New York, N.Y.

[21] Appl. No.: 703,778

[22] Filed: Feb. 21, 1985

[51] Int. Cl.$^4$ ........................................... C07D 487/14
[52] U.S. Cl. ................................................... 548/422
[58] Field of Search ...................................... 548/422

[56] References Cited

U.S. PATENT DOCUMENTS

| | | | |
|---|---|---|---|
| 4,156,735 | 5/1979 | Lang et al. | 544/278 X |
| 4,246,269 | 6/1981 | Paioni | 514/328 X |
| 4,264,504 | 4/1981 | Urakawa et al. | 548/422 |
| 4,478,769 | 12/1984 | Vyas et al. | 548/422 X |

OTHER PUBLICATIONS

Mullin, *Crystallization*, Butterworth & Co. Limited, London (1961), pp. 107–109.

*Primary Examiner*—Donald G. Daus
*Assistant Examiner*—William A. Teoli, Jr.
*Attorney, Agent, or Firm*—David M. Morse

[57] ABSTRACT

There is disclosed a new crystalline form of 7-(dimethylaminomethylene)amino-9a-methoxymitosane having an infra-red spectrogram as disclosed in the drawing. This new crystalline form is characterized by substantially greater storage stability than amorphous 7-(dimethylaminomethylene)amino-9a-methoxymitosane.

3 Claims, 1 Drawing Figure

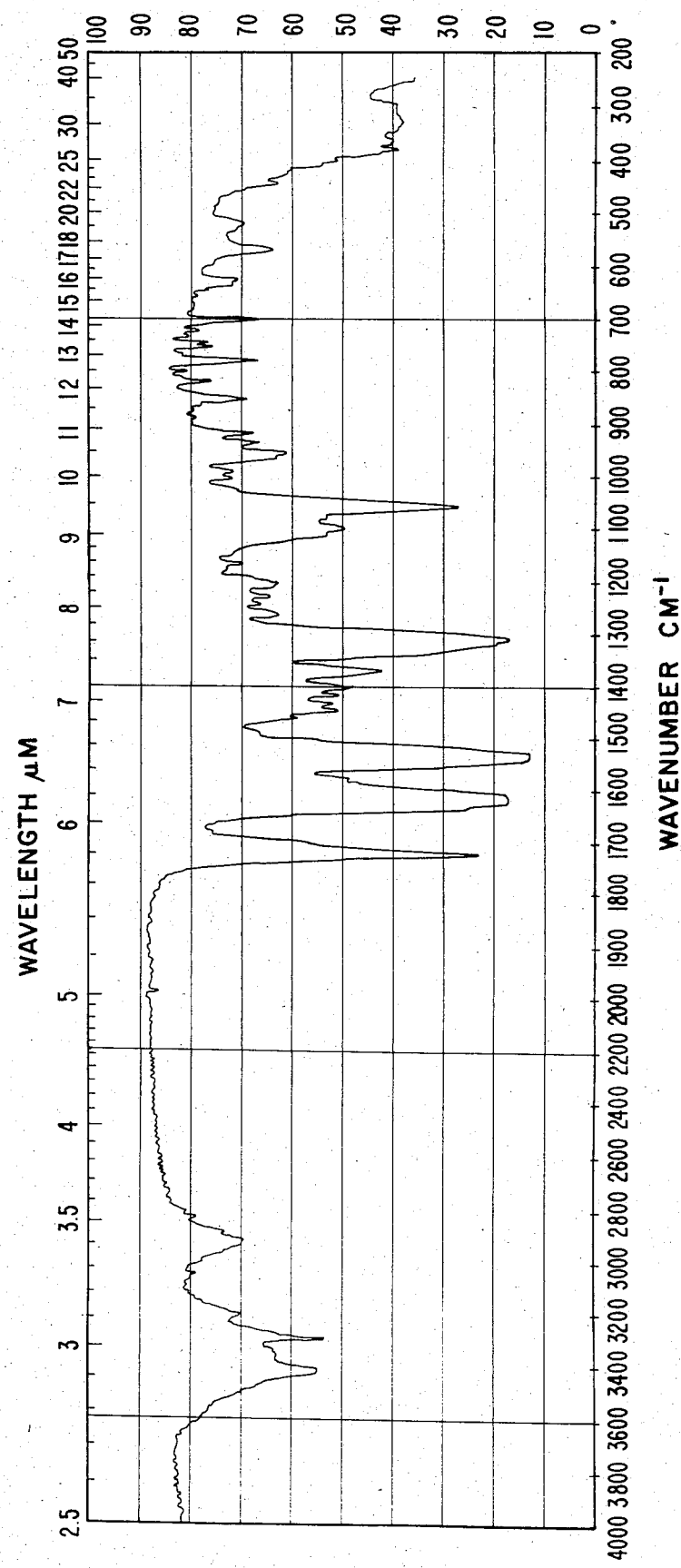

CRYSTALLINE FORM OF 7-(DIMETHYLAMINOMETHYLENE-AMINO-9A-METHOXYMITOSANE

FIELD OF THE INVENTION

The present invention relates to a novel, crystalline form of 7-(dimethylaminomethylene)amino-9a-methoxymitosane which is stable, even at temperatures up to 100° C.

DESCRIPTION OF THE PRIOR ART

Mitomycin C is an antibiotic which is produced by fermentation and is presently on sale under Food and Drug Administration approval to the therapy of disseminated adenocarcinoma of the stomach or pancreas in proven combinations with other approved chemotherapeutic agents and as palliative treatment when other modalities have failed (Mutamycin ® Bristol Laboratories, Syracuse, N.Y. 13201, Physicians' Desk Reference 38th Edition, 1984, p. 750). Mitomycin C and its production by fermentation is the subject of U.S. Pat. No. 3,660,578 patented May 2, 1972 claiming priority from earlier applications including an application filed in Japan on Apr. 6, 1957.

The structures of mitomycins A, B, C, and of porfiromycin were first published by J. S. Webb et al of Lederle Laboratories Division American Cyanamid Company, J. Amer. Chem. Soc. 84, 3185–3187 (1962). One of the chemical transformations used in this structure study to relate mitomycin A and mitomycin C was the conversion of the former, 7,9a-dimethoxymitosane, by reaction with ammonia to the latter, 7-amino-9a-methoxymitosane. Displacement of the 7-methoxy group of mitomycin A has proven to be a reaction of considerable interest in the preparation of antitumor active derivatives of mitomycin C. The following articles and patents each deals with the conversion of mitomycin A to a 7-substituted amino mitomycin C derivative having antitumor activity.

Matsui et al "The Journal of Antibiotics", XXI, 189–198 (1968)

Kinoshita et al "J. Med. Chem." 14, 103–109 (1971)

Iyengar et al "J. Med. Chem." 24, 975–981 (1981)

Iyengar, Sami, Remers, and Bradner, Abstracts of Papers—Annual Meeting of the American Chemical Society, Las Vegas, Nev., March 1982, Abstract No. MEDI 72.

Sasaki, et al Internat. J. Pharm., 1983, 15, 49.

The following patents deal with the preparation of 7-substituted aminomitosane derivatives by the reaction of mitomycin A, mitomycin B, or an $N^{1a}$-substituted derivative thereof with a primary or secondary amine:

Cosulich et al, U.S. Pat. No. 3,332,944, patented July 25, 1967.

Matsui et al, U.S. Pat. No. 3,420,846, patented Jan. 7, 1969.

Matsui et al, U.S. Pat. No. 3,450,705, patented June 17, 1969.

Matsui et al. U.S. Pat. No. 3,514,452, patented May 26, 1970.

Nakano et al, U.S. Pat. No. 4,231,936, patented Nov. 4, 1980.

Remers, U.S. Pat. No. 4,268,676, patented May 19, 1981.

Mitomycin C derivatives having a substituted amino substituent in the 7-position have also been prepared by directed biosynthesis, that is by supplementing fermentation broths with a series of primary amines, and carrying out the conventional mitomycin fermentation (C. A. Claridge et al Abst. of the Annual Meeting of Amer. Soc. for Microbiology 1982. Abs. 028).

Belgian Pat. No. 896,963, the disclosure of which is incorporated herein by reference, discloses a novel group of monoguanidino, or mono- and bis-amidino analogs of mitomycin C in which either or both the 7-amino nitrogen atom and the $N^{10}$ carbamoyl nitrogen atom of mitomycin C are part of an amidino substituent or the 7-amino nitrogen is part of a guanidino group. One such compound, prepared as described in Examples 8 and 15 of that patent, is the compound 7-(dimethylaminomethylene)amino-9a-methoxymitosane which has the following structure:

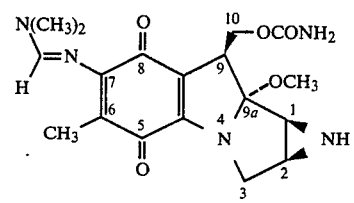

This compound, obtained as an amorphous solid, has a high activity against P-388 murine leukemia, exceeding that of mitomycin C both in terms of maximum effect and milligram potency (comparative dosage sizes for equivalent effects). However, it is generally unstable at 25°–56° C.

SUMMARY OF THE INVENTION

A crystalline form of 7-(dimethylaminomethylene)amino-9a-methoxymitosane has now been found which is stable even at temperatures up to 100° C. for six days or longer. It has an infra-red spectrogram as disclosed in the drawing and possesses substantially greater storage stability than amorphous 7-(dimethylaminomethylene)amino-9a-methoxymitosane.

DETAILED DESCRIPTION OF THE INVENTION

Amorphous 7-(dimethylaminomethylene)amino-9a-methoxymitosane is prepared by the procedures of Examples 8 and 15 of Belgian Pat. No. 896,963. These procedures are described below.

Procedure of Example 8 of Belgian Pat. No. 896,963

Compound I, 7-[(dimethylamino)methylene]amino-$N^{10}$-(dimethylamino)methylene-9a-methoxymitosane, was prepared as follows:

To a suspension of 500 mg (1.50 mM) of mitomycin C in 25 ml chloroform was added in total 9.6 ml (2.4 ml portions at 0, 18, 21 and 23 hours) of N,N-dimethylformamide dimethyl acetal and the suspension was stirred at about 50° C. for 41 hours. Upon evaporation of the solvent and excess reagent under reduced pressure, a dark green residue was obtained; tlc (methylene chloride/methanol 20:1) revealed the absence of mitomycin C and the presence of two new green components (Rf=0.16 and 0.22). The major component (Rf=0.16) was isolated by flash chromatography; using methylene chloride/methanol 20:1 as the eluant, as a green solid (340 mg 51.5%), which upon dissolution in diethyl ether followed by an addition of hexane afforded Compound I as a dark green amorphous powder.

NMR (pyridine d$_5$, δ); 2.18 (s, 3H), 2.70 (bs, 1H), 2.76 (s, 3H), 2.82 (s, 3H), 2.86 (s, 6H), 3.22 (s, 3H), 3.30 (bs, 1H), 3.60 (d, J=12 Hz), 4.12 (dd, 1H, J=10, 4 Hz), 4.43 (d, 1H, J=12 Hz), 4.90 (bs, 1H), 5.10 (t, 1H, J=10 Hz), 5.52 (dd, 1H, J=10, 4 Hz), 7.85 (s, 1H), 8.64 (s, 1H).

IR(KBr)$\nu_{max}$ cm$^{-1}$: 3300, 2930, 1675, 1620, 1545, 1230, 1060.

UV(H$_2$O)$\lambda_{max}$ nm: 390 and 244

Analysis: Calc'd for C$_{21}$H$_{28}$N$_6$O$_5$: C, 56.71; H, 6.08; N, 18.90 Found: C, 56.20; H, 6.28; N, 17.88.

7-(Dimethylaminomethylene)amino-9a-methoxymitosane (II) was prepared as follows:

To compound I (600 mg, 1.35 mM) dissolved in methanol (10 ml) was added aminodiphenylmethane (2.2 ml, 10.8 mM) and the resulting solution was stirred at 54° C. for 4 hours. The progress of the reaction was monitored by tlc (methylene chloride/methanol 90:10). At the end of 4 hours the starting material (RF=0.35) had disappeared and a major new green zone (Rf=0.29) appeared instead. The solution was concentrated at reduced pressure and the resulting syrup was flash chromatographed (25 g silica gel) using methylene chloride/methanol 20:1 as the eluant. Fractions containing the green component (Rf=0.29) were pooled, dried (Na$_2$SO$_4$) and concentrated. Compound II was obtained as an amorphous solid (215 mg, 41%).

NMR (pyridine d$_5$, δ): 2.18 (s, 3H), 2.70 (bs, 1H), 2.80 (s, 3H), 2.88 (s, 3H), 3.08 (bs, 1H), 3.24 (s, 3H), 3.56 (bd, 1H, J=12 Hz), 4.00 (dd, 1H), 4.44 (d, 1H, J=12 Hz), 5.06 (t, 1H, J=10 Hz), 5.56 (dd, 1H, J=10, 4 Hz), 7.58 (bs, 2H), 7.88 (s, 1H).

IR(KBr)$\nu_{max}$ cm$^{-1}$: 3300-3450, 2960-2910, 1715, 1620, 1535, 1050

UV(H$_2$O)$\lambda_{max}$ nm: 390 and 226

Anal. Calc'd for C$_{18}$H$_{23}$N$_5$O$_5$: C, 55.48; H, 5.91; N, 17.98 Found: C, 54.83; H, 5.67; N, 16.90.

Procedure of Example 15 of Belgian Pat. No. 896,963

A 0.5M solution of N,N-dimethylchloromethyleniminium chloride was prepared by dropwise addition of oxalyl chloride (1.57 g. 12.5 mmol) at 0° C. to a solution of dimethylformamide (915 mg. 12.5 mmol) in 25 ml of CHCl$_3$ followed by stirring at room temperature for 30 minutes. Separately, a solution of mitomycin C (334 mg, 1 mmol) in 5 ml of dimethylformamide was added to a suspension of NaH (36 mg, 1.5 mmol) in 3 ml of dimethylformamide. The solution was stirred at room temperature for 20 minutes and cooled to −40°~−50° C. and the above solution of N,N-dimethylchloromethyleniminium chloride (3 ml, 1.5 mmol) was then added. Additional NaH (18 mg, 0.75 mmol) was added after 10 minutes of stirring at −40° C. The solution was kept at −40° C. for 1 hour and then diluted with CH$_2$Cl$_2$ and filtered. The residue obtained after evaporation of the filtrate was chromatographed by thin layer chromatography (TLC) on silica gel (10% CH$_3$OH—CH$_2$Cl as elutant). Extraction of the major green band yielded 78 mg (43% based on the recovered mitomycin C) of an amorphous solid whose NMR spectrum and TLC behavior were identical to those of Compound II prepared as described above.

Amorphous 7-(dimethylaminomethylene)amino-9a-methoxymitosane can be converted to the crystalline form by dissolving it in acetone and/or ethanol and adding this solution to ether. It is preferred to add the solution over an extended period of time, e.g., 20 minutes. An alternative procedure for the preparation of crystalline 7-(dimethylaminomethylene)amino-9a-methoxymitosane is to slurry a quantity of amorphous 7-(dimethylaminomethylene)amino-9a-methoxymitosane in ethyl ether and then to add a small amount of crystalline 7-(dimethylaminomethylene)amino-9a-methoxymitosane. This results in transformation of the amorphous 7-(dimethylaminomethylene)amino-9a-methoxymitosane to the crystalline form.

DESCRIPTION OF SPECIFIC EMBODIMENTS

The following examples constitute detailed procedures for the preparation of crystalline 7-(dimethylaminomethylene)amino-9a-methoxymitosane.

EXAMPLE 1

Amorphous 7-(dimethylaminomethylene)amino-9a-methoxymitosane free-base (1.0 g.) was dissolved in 10 ml of acetone. The acetone solution was added over a 20 minute interval to 100 ml of ether while rapidly stirring. Crystals were observed to form. The crystalline mass was slurried for 24 hours at 20°-25° C. in a closed system. The dark-green crystals were then removed via vacuum filtration. The crystals were washed with 10 ml of ether, and 15 ml of Skellysolve-B and were high-vacuum dried at 40° C. for 24 hours. Yield: 0.75 g.

Anal. Calc'd for C$_{18}$H$_{23}$N$_5$O$_5$: C, 55.48; H, 5.91; N, 17.98 Found: C, 55.11, 55.37; H, 5.88, 5.93; N, 17.6, 17.7.

This material was found to have an infra-red spectrogram as disclosed in the drawing. The infra-red spectrum was recorded from a sample in a pressed potassium bromide disc. A nuclear magnetic resonance spectrum (NMR) was determined at 90 MHz for proton ($^1$H NMR). The NMR spectrum had the following J values:

| ppm δ | Description | Integral | Assignments |
|---|---|---|---|
| 1.86 | Singlet | 3 | CH$_3$— |
| 2.73 | Doublet of doublet | 1 (J = +1.8 Hz; 4.4 Hz) | C$_2$H |
| 2.83 | Doublet | 1 (J = 4.4 Hz) | C$_1$H |
| 2.97 | Singlet | 3 | |
| 3.01 | Singlet | 3 | N(CH$_3$)$_2$ |
| 3.14 | Singlet | 3 | OCH$_3$ |
| 3.43 | Doublet of doublets | 1 (J = 1.8 Hz; J = 12.8 Hz) | C$_3$H |
| 3.54 | Doublet of doublets | 1 (J = 4.4 Hz; J = 10.7 Hz) | C$_9$H |
| 4.10 | Doublet | 1 (J = 12.8 Hz) | C$_3$H |
| 4.42 | Triplet | 1 (J = 10.7 Hz) | CH$_2$O |
| 4.69 | Doublet of doublets | 1 (J = 4.4 Hz; J = 10.7 Hz) | CH$_2$O |
| 4.76 | Broad singlet | 2 | NH$_2$ |
| 7.21 | Solvent singlet (CHCl$_3$) | | |
| 7.62 | Singlet | 1 | H—C≡N |

An ultraviolet spectrum run on a solution of 0.01625 g. of the material per liter of methanol had the following characteristics:

| λ max (nm) | Absorptivity (a) | Molar Absorptivity (ε) | Log ε |
| --- | --- | --- | --- |
| 232 | 47.8 | 18610 | 4.27 |
| 386 | 43.0 | 16740 | 4.22 |

EXAMPLE 2

Amorphous 7-(dimethylaminomethylene)amino-9a-methoxymitosane free-base (1.0 g.) was slurried in 10 ml of ethyl ether. A small amount of crystalline 7-(dimethylaminomethylene)amino-9a-methoxymitosane obtained in Example 1 (approximately 2 mg.) was added to the mixture, and the mixture was slurried in a closed system for 48 hours at 20°–25° C. Following this time, the resultant dark-green crystals were removed via vacuum filtration. The crystals were washed with 10 ml of ether, 15 ml of Skellysolve-B and dried under high vacuum at 40° C. for 24 hours. Yield: 0.9+g. The crystalline product had the same properties as did the product obtained in Example 1.

The stability of crystalline 7-(dimethylaminomethylene)amino-9a-methoxymitosane was determined by the following procedure: a precise amount of 7-(dimethylaminomethylene)amino-9a-methoxymitosane ranging from 5–25 mg is placed in as many 1-dram screw cap vials as required. The required amounts of screw cap vials containing the accurately weighed 7-(dimethylaminomethylene)amino-9a-methoxymitosane are placed at the varied temperature stations. At each time-temperature interval, a vial containing the pre-weighed 7-(dimethylaminomethylene)amino-9a-methoxymitosane is submitted for HPLC assay. The assay is reported as mcg/mg of 7-(dimethylaminomethylene)amino-9a-methoxymitosane activity. The results are set forth in Table 1. In this table, the numbers set forth in parentheses are the percent losses for amorphous 7-(dimethylaminomethylene)amino-9a-methoxymitosane.

TABLE 1

| Time in Days | Percent Loss | | | |
| --- | --- | --- | --- | --- |
| | 45° C. | 56° C. | 85° C. | 100° C. |
| 1 | | | | 0–1 |
| 3 | | | (93) | |
| 4 | | | | 0 |
| 5 | | | | 0(100) |
| 6 | | | | 3.2 |
| 7 | | 0(14) | | |
| 14 | | 0(25) | | 2.8, 4.8, 9.7 |
| 30 | 0 | 0(41) | | |

What is claimed is:

1. A new crystalline form of 7-(dimethylaminomethylene)amino-9a-methoxymitosane having an infrared absorption spectrum (potassium bromide disc) exhibiting principal absorption peaks at 3430, 3310, 2920, 1720, 1620, 1540, 1455, 1440, 1420, 1400, 1375, 1310, 1270, 1230, 1205, 1100, 1065, 950, 850, 780, 700, 625, 575, and 525 reciprocal centimeters.

2. A process for preparing crystalline 7-(dimethylaminomethylene)amino-9a-methoxymitosane which comprises dissolving amorphous 7-(dimethylaminomethylene)amino-9a-methoxymitosane in acetone and/or ethanol and adding the solution to ether.

3. A process for preparing crystalline 7-(dimethylaminomethylene)amino-9a-methoxymitosane which comprises slurrying amorphous 7-(dimethylaminomethylene)amino-9a-methoxymitosane in ethyl ether and thereafter adding a small amount of crystalline 7-(dimethylaminomethylene)amino-9a-methoxymitosane to cause crystallization of the amorphous 7-(dimethylaminomethylene)amino-9a-methoxymitosane.

* * * * *